United States Patent [19]

Winn

[11] 4,373,009
[45] Feb. 8, 1983

[54] METHOD OF FORMING A HYDROPHILIC COATING ON A SUBSTRATE

[75] Inventor: R. Alastair Winn, Santa Barbara, Calif.

[73] Assignee: International Silicone Corporation, San Diego, Calif.

[21] Appl. No.: 264,957

[22] Filed: May 18, 1981

[51] Int. Cl.³ ............................................. A61M 25/00
[52] U.S. Cl. .............................. 428/424.2; 428/424.4; 428/423.5; 428/424.6; 427/412.1; 427/2; 604/8; 604/280
[58] Field of Search ............... 428/424.2, 424.4, 224.8, 428/423.5, 424.7, 424.6; 427/412.1, 2; 128/348, 349 R

[56] References Cited

U.S. PATENT DOCUMENTS

| | | | |
|---|---|---|---|
| 2,911,321 | 11/1959 | Herrmann | 428/424.8 |
| 3,005,728 | 10/1961 | Bridgeford | 428/424.8 |
| 3,023,126 | 2/1962 | Underwood | 428/424.2 |
| 3,198,692 | 8/1965 | Bridgeford | 428/424.2 |
| 4,020,216 | 4/1977 | Miller | 428/424.2 |
| 4,119,094 | 10/1978 | Micklus | 428/424.8 |

*Primary Examiner*—Sam Silverberg
*Attorney, Agent, or Firm*—Donald D. Mon; David O'Reilly

[57] ABSTRACT

A method of forming a hydrophlic coating on a substrate comprised of applying a hydrophilic copolymer capable of chemically reacting with a coupling agent which will promote adhesion to the substrate. A polyisocyanate coupling agent is applied to the surface from a solvent solution followed by applying the hydrophilic copolymer from solvent solution. In certain instances, the copolymer and isocyanate can be simultaneously applied from a solvent solution. The resulting hydrophilic coating is thrombo resistant, biocompatable and stable.

56 Claims, No Drawings

METHOD OF FORMING A HYDROPHILIC COATING ON A SUBSTRATE

FIELD OF THE INVENTION

This invention relates to methods of coating substrates with a hydrophilic copolymer and in particular for producing hydrophilic coatings on substrates used in biomedical applications.

BACKGROUND OF THE INVENTION

The formation of hydrophilic coatings on substrates has many applications but in particular is most desirable in many biomedical applications. For example, biomedical applications such as wound drains, catheters, surgical tools and arteriovenous shunts, an article having a hydrophilic surface coating is desirable to minimize thrombosis, crystal formation, tissue trauma, tissue adhesion to surgical instruments, and foreign body reactions. In prior art methods, surfaces have been rendered hydrophilic by such methods as high energy radiation in situ polymerization processes, by direct chemical bonding or by forming interpolymer networks. The radiation process can render a very stable hydrophilic surface, but suffers from unreliable results and can produce radiation damage to the substrate. Formation of interpolymer networks also produces hydrophilic surfaces but in turbulent flow or extended soaking, the interpolymer networks often break down and the hydrophilic portion can be washed away rendering the substrate surface defective.

Prior art methods described using a polyurethane coating agent to adhere poly-N-vinyl pyrollidone (PVP) to various substrates, thus producing an article having a hydrophilic coating of low coefficient friction. Extensive studies indicate, however, that in turbulent flow or upon extended soaking in aqueous media, the hydrophilic coating can be leeched off, thus rendering the article insufficiently hydrophilic. The prior art depended upon non-covalent bonds and interpolymer networks produced to achieve coating stability. These methods of adhering a hydrophilic polymer such as PVP to a substrate surface coated with a urethane have not achieved the degree of coating stability required for many applications, particularly biomedical drains, catheters, and blood invasive devices.

SUMMARY OF THE INVENTION

The purpose of the present invention is to provide a hydrophilic coating on a substrate which is stable.

While experimenting with hydrophilic polymer coatings bonded to various substrates, the applicant unexpectedly found that hydrophilic polymers or copolymers containing active hydrogens show exceptional stability and resistance to hydrosis when coupled to the substrate with isocyanate systems. It was subsequently determined that the stability arises from the covalent bonding of hydrophilic polymer with isocyanates. An advantage of this process is that a simple and effective treatment can render an article having an extremely stable hydrophilic coating.

The invention comprises coating a substrate with a polyisocyanate and a hydrophilic copolymer having pendant groups which react with the isocyanates. The polyisocyanate and the hydrophilic copolymer produce a covalent graft or bond between the hydrophilic coupling agent and the hydrophilic copolymer. The method described hereinafter is suitable for use with a variety of polymer substrates to which conventional isocyanate cured coatings adhere. In the method of the invention a polyisocyanate in a solvent solution is applied to the surface of a substrate to be coated with the hydrophilic copolymer by dripping, spraying or the like and then evaporating the solvent preferably by air drying. This step forms a coating with unreacted isocyanate groups on the surface of the substrate. A copolymer having an average of at least two active hydrogen atom sites per molecule is then applied to the surface of the substrate and reacts with the unreacted isocyanate groups to produce a covalently bound matrix, thus forming a stable hydrophilic coating.

In another method of the invention, the hydrophilic copolymer and polyisocyanate can be applied from solvent simultaneously. Thus the polyisocyanate can crosslink the copolymer to the substrate and to itself. Extended soaking to form better interpenetrating polymer networks between substrate and hydrophilic network may improve bonding in this method.

It is one object of the present invention to provide a method forming an extremely stable hydrophilic coating on a substrate surface.

Yet another object of the present invention is to provide a method of producing a covalent bond between a hydrophilic copolymer and coupling agent to produce an extremely stable hydrophilic surface on a substrate.

Still another object of the present invention is to provide a method of forming a hydrophilic surface on a substrate in which the coupling agent and copolymer are simultaneously applied from a solvent solution.

Yet another object of the present invention is to provide a method of applying a hydrophilic coating on a variety of substrates.

Still another object of the present invention is to provide a method of applying a hydrophilic surface to a substrate used in biomedical applications.

These and other objects of the present invention become apparent from the following detailed description of the invention.

DESCRIPTION OF THE PREFERRED EMBDOIMENT

The present invention is a method of forming a hydrophilic coating on a surface of the substrate which the substrate is first coated with a curing agent and then reacted with a copolymer to produce a covalent bond between the coupling agent and the hydrophilic copolymer. Generally, the substrates may be any one of a variety of materials but preferably is in the form of a polymer which is easily reacted with the curing agent and the hydrophilic copolymer.

The method of the invention comprises first applying a solvent solution containing a polyisocyanate to the surface of the substrate to be coated with the hydrophilic copolymer by dipping, spraying or the like, and then evaporating the solvent preferably by air drying. This step forms a coating with unreacted isocyanate groups on the substrate. The unreacted isocyanate groups are then available for covalent bonding to a copolymer which will be described in greater detail hereinafter.

The substrate may be any suitable material to which cured isocyanates adhere. The use of isocyanate croslined adhesive systems is well known in the art. (see Handbook for Adhesives, Irving Skeist, ed. 1977 herein incorporated by reference). Isocyanate coupling agents bond well to such substrates as glass, aluminum, steel, polyesters, polyvinylchlorides, butadiene, styrene, latex rubber, nylon, polycarbonate and polyurethane. It is preferred to use polymer substrates such as polyurethane resin, a vinyl resin such as polyvinylchloride, a polyacrylate such as polymethylmethacrylate, a polycarbonate, a polyester such as polyethylene terrephthalate, polybutylene terrephthalate, polytetramethylene terraphthlate, or a rubber such as a latex rubber, polyisoprene or butadiene styrene copolymer. In addition, it has been reported that conventional urethanes can be used in conjunction with polyisocyanates to improve adhesion.

Alternatively, a polyurethane selected from a wide variety of compounds may be added. Examples of a polyurethane is the reaction product of 2,4-toluene diisocyanate and position isomers thereof, 4,4''-diphenylmethane diisocyanate and position isomers thereof, polymethylene-polyphenyl isocyanate, or 1,5-napthylene diiosocyanate with 1,2-polypropylene glycol, polytetramethylene ether glycol, 1,4-butanediol, 1,4-butylene glycol, 1,3-butylene glycol, poly (1,4-oxybutylene) glycol, caprolactone, adipic acid esters, phthalic anhydride, ethylene glycol, 1,3-butylene glycol, 1,4-butylene glycol or diethylene glycol. For further examples see Encyclopedia of Polymer Sciences and Technology cited hereinabove.

Among the preferred polyurethanes are conventional polyurethanes polytetramethylene ether glycol-diphenylmethane diisocyanate (TDI), polytetramethylene ether glycol-isoferrone isocyanate, poly (1,3-oxybutylene) glycoldiphenylmethane diisocyanate (MDI), poly (1,4-oxybutylene) glycol-toluene diisocyanate (TDI), poly (1,4-oxybutylene) glycoltolisoferrone isocyanate, polyethylene glycol-toluene diisocyanate (TDI), polyethylene glycol-isoferrone isocyanate, polypropylene glycoldiphenylmethane diisocyanate (MDI), polypropylene glycol-toluene diisocyanate (TDI), polypropylene glycolisoferrone isocyanate, polycaprolactone-diphenylmethane diisocyanate (MDI), polycaprolactone-toluene diisocyanate (TDI), polycaprolactone-isoferrone isocyanate, polyethylene adipate-diphenylmethane diisocyanate (MDI), polyethylene adipate-toluene diisocyanate (TDI), polyethylene adipate-isoferrone isocyanate, polytetramethylene adipate-diphenylmethane diisocyanate (MDI), polytetramethylene adipate-toluene diisocyanate (TDI), polytetramethylene adipate-isoferrone isocyanate, polyethylenepropylene adipatediphenylmethane diisocyanate (MDI), polyethylene-propylene adipate-toluene diisocyanate (TDI), and polyethylene-propylene adipateisoferrone isocyanate polyurethanes.

Chain extenders may also be used with hydrogen containing difunctional compounds such as water, diamines, or amino acids. Examples of such chain extenders are 1,3-butanediol, hexamethylene diamine, 4,4-methylene-bis (2-chloronalinine) (MOCA), trimethulolpropane, and ethanolamine. Other additives include accelerators, catalysts, stabilizers, plasticizers, or the like which improve or modify the properties of the urethane may also be used. Examples of such additives are dicumyl peroxide, benzothiazyldisulfide, mercapto benothiazole, benzothiazole disulfide, polypropylene adiapate and metal salts such as potassium acetate, cobalt naphthenate, and zinc chloride.

Low surface energy materials (less than 32 dynes/cm$^2$) such as polytetraflouroethane, polypropylene, polyethylene, and silicone typically do not bond well with polyisocyanate systems. Bonding to low surface energy materials can be improved by solvent aided interpolymer networks or by modifying the exposed surface with radiation, oxidizing agents such as ozonolysis or coupling agents such as gamma-amino propyl triethoxy silane.

The polyisocyanate may be selected from a variety of compounds. Examples of these are polymethylenepolyphenyl isocyanate, 4,4'-diphenylmethane diisocyanate and position isomers thereof, 2,4-toluene diisocyanate and position isomers thereof, 3,4-dichlorophenyl diisocyanate and isoferrone isocyanate. Adducts or prepolymers of isocyanates and polyols such as the adduct of trimethylolpropane and diphenylmethane diisocyanate or toluene diisocyanate are suitable. For further examples of polyisocyanates see Encyclopedia of Polymer Science and Technology, H. F. Mark, N. G. Gaylord and N. M. M. Bikales (eds.), (1969) incorporated herein by reference.

Other isocyanates which could be used are those known as "blocked" isocyanates. Blocked isocyanates can be used in media containing solvents which would react with straight isocyanates. Thus the hydrophilic copolymer could be applied from alcohol, water, or amino functional solvents without consuming isocyanates reactive sites. Examples of a blocked isocyanate are phenol blocked diphenylmethane 4,4'-diisocyanate, (Hylene MP FROM Dupont), ketoxime blocked tetraisocyanate (E-320 Mobay).

The solvent used to apply the coupling agent is one which will not react with isocyanates, i.e., it should be free of reactive amino, hydroxyl and carboxyl groups. Preferred solvents are dichloromethane, methyl ethyl ketone, acetone, ethyl lactate, chloroform, trichloroethylene and ethyl acetate. The ethyl lactate has a hydroxyl but is not sufficiently reactive to be detrimental. So called "reactive diluents" may also be used. In this case, the diluents are reacted after the dipping operation. Thus the need to evaporate all or part of the solvent is eliminated. Examples of reactive diluents are N-vinyl-2-pyrollidone, hydroxy methyl methacrylate, butylene glycol dimethacrylate. Exposing these reactive diluents to ultraviolet light in the presence of an activator such as benzophenone will cause them to polymerize and crosslink in situ, thus contributing to the hydrophilic polymer content.

The solvent solution applied to the substrate is advantageously a solution in which a polyisocyanate will be from about a minimum of 0.1% W/V (Weight to Volume), and preferably from about 0.3% to about 5% W/V.

Alternatively a polyurethane in the solution, if used, can be from about 0.3% to about 10% W/V (Weight to Volume), and preferably from about 0.3% to about 4% W/V.

While the substrate surface generally need be in contact with the coupling agent solution only briefly, for example 1–4 minutes, in the case of the rubber latex substrate, a longer period from about 15 to 20 minutes or more is desirable to achieve firm adherence of the final interpolymer coating to the rubber latex. Also with a rubber latex substrate, a pretreatment step of soaking the rubber latex in a a suitable solvent such as a chlorinate hydrocarbon solvent, methylene chloride, chloroform, 1,1,1-trichloroethane, and ethylene chloride is desirable. For example, 15 to 120 minutes or more to swell the rubber, is advantageous.

The copolymer used for providing the hydrophilic coating may consist of a variety of repeating units. The primary requirement of the copolymer is that it be swellable, and preferably soluable in an aqueous media and contain a minimum average of two active hydrogen atom sites per molecule. Functional groups containing active hydrogen atoms capable of reacting with isocyanates include —OH (hydroxyl), —SH (sulfhydral), —NH—(imino), —NH$_2$ (amino), —NHCO—O— (carbamate), —NHR (substituted amino), —NHCONH— (carbamide), —COOH (carboxyl), —CONH$_2$(carbonamide), —CONHR— (substituted carbonamide), —CSNH$_2$ (thioamide), —SO$_2$OH (sulfonic), etc.

Ideally, the copolymer selected should also be soluble in a non-aqueous solvent which does not react with isocyanates. Examples of such solvents are methyl ethyl ketone, chloroform and ethyl lactate.

Another preferably characteristic os the copolymer is that it should consist of units containing no reactive hydrogen atoms, such as vinyl methyl ether, vinyl pyridine or N-vinyl-2-pyrrolidone and a lesser number of units containing active hydrogen atoms such as acrylamide, hydroxy acrylate, acrylic acid, hydroxy propylemethacrylate, or hydroxy ethyl methacrylate. The list of potential monomers is very large and one experienced in the art could easily identify thousands of combinations. Polymerization of the copolymer can be achieved by many suitable methods including chemical free radical initiators such as benzoyl peroxide or azo-bisisobutyronitrile, ultraviolet light and activators such as benzophenone, or high energy radiation. Ideally the molecular weight average should exceed 100,000.

The hydrophilic copolymer solution should contain sufficient solids to deposit a layer of copolymer a minimum thickness of 500 angstroms. Ideally, the copolymer coating should be between 5000 and 100,000 angstroms. Thicker coatings may be used, but the copolymer may be more easily leached as the distance between the coupling coat and the opposite side of the applied hydrophilic coat increase. Coating thicknesses in excess of 100,000 angstroms show no known advantage over thinner coatings.

In the preferred method, the substrate surface is treated in two steps. The substrate is first coated with polyisocyanate as described above. The substrate, containing unreacted isocyanates, is then coated with the hydrophilic copolymer solution and allowed to dry and cure at room or elevated temperature. A film of hydrophilic polymer is thus coupled to the substrate.

In yet another method of this invention, the polyisocyanate and the hydrophilic copolymer can be applied to the substrate from the same solvent solution. The reaction of isocyanates subsequently crosslinks and couples the hydrophilic copolymer to the substrate.

EXAMPLE 1

100 grams N-vinyl-2-pyrollidone and 1 gram acrylamide were polymerized by exposing the mixture to 5 M rads from a high energy electron beam source. The resultant molecular weight of the copolymer was determined to be approximately 300,000. This copolymer was then dissolved in an ethyl lactate at 3% solids.

EXAMPLE 2

A clean piece of vinyl tubing was dipped into a solution containing 0.25% (weight/weight) of the adduct of trimethylolpropane diphenylmethane diisocyanate in methyl ethyl ketone. The tube was removed after 20 minutes and dried for 5 minutes at 60° C.

The treated tubing was then dipped in the copolymer solution of Example 1. Another tube was treated identically except the polymer solution from Example 1 was replaced with a 3% solution of polyvinylpyrollidone PVP (K90) in ethyl lactate.

The tubes were then dried and cured one hour at 70° C. Coating thickness was determined to be approximately 30,000 angstroms.

Upon immersion in water at 37° C., both treatments demonstrated a hydrophilic surface. After soaking 60 minutes, the copolymer tube was unchanged but the coating on the PVP homopolymer coated tube could be easily rubbed off with finger pressure. This shows the covalently coupled copolymer renders a more stable hydrophilic coating by the method described.

EXAMPLE 3

The vinyl tubing treated with hydrophilic copolymer in Example 2 was tested for thrombo-resistance by a modified Lee-White Clotting Time Test (Journal of Biomedical Material Research, Wollin, R. F., 1972 incorporated herein by reference), along with untreated vinyl, silicone and glass control tubes. The clotting times were reported as follows:

Vinyl tubing: 10 minutes
Glass: 5 minutes
Silicone: 15 minutes
Hydrophilic Copolymer: 20 minutes plus.

The hydrophilic coating clearly shows an advantage in resistance to clotting.

This invention is not to be limited by the embodiment described in the description, which is given by way of example and not of limitation, but only in accordance with the scope of the appended claims.

I claim:

1. The method of bonding a hydrophilic coating to the surface of a biomedical substrate comprising:
   applying a coating from a solvent solution comprised of a polyisocyanate to the surface of said substrate to form a coupling coating with unreacted isocyanates;
   applying a solvent solution comprised of a hydrophilic copolymer made from monomers of vinylpyrollidone and monomers containing active hydrogen which will react with isocyanate to form a covalent bond between said coupling coating and said hydrophilic copolymer;
   evaporating the solvent and reacting said isocyanates.

2. The method according to claim 1 in which said substrate is a polymer substrate.

3. The method according to claim 2 in which said polymer substrate is selected from the group consisting of a polyurethane resin, a vinyl resin, a polyacrylate, a polycarbonate, a polyester and rubber.

4. The method according to claim 3 in which said rubber is selected from the group consisting of latex rubber, polyisoprene and butadiene styrene copolymer.

5. The method according to claim 1 in which said polyisocyanate is selected from the group consisting of polymethylenepolyphenyl isocyanate, 4,4'-diphenylmethane diisocyanate and position isomers thereof, 3,4-dichlorophenyl diisocyanate and isoferrone isocyanate.

6. The method according to claim 1 in which said polyisocyanate is a blocked isocyanate.

7. The method according to claim 6 in which said polyisocyanate is selected from the group consisting of phenol blocked diphenyl methane 4,4′-diisocyanate, and ketoxime blocked tetraisocyanate (E-320 Mobay).

8. The method according to claim 1 in which said copolymer has an average of at least two active hydrogen atom sites per molecule.

9. The method according to claim 8 in which said copolymer is swellable in an aqueous media.

10. The method according to claim 9 in which said copolymer is also soluble in non-aqueous solvents which do not react with isocyanate.

11. The method according to claim 8 in which said copolymer consists primarily of repeating units containing no reactive hydrogen atoms.

12. The method according to claim 8 in which said copolymer is selected from the groups consisting of vinyl methyl ether, vinyl pyridine, N-vinyl-2-pyrrolidone, acrylamide, hydroxy acrylate, acrylic acid hydroxy propyl methacrylate and hydroxy ethyl methacrylate.

13. The method according to claim 1 in which said polyisocyanate is at least about 0.1% W/V.

14. The method according to claim 13 in which said polyisocyanate is from about 0.3% to about 15% W/V.

15. The method according to claim 2 in which said polyisocyanate solution is in contact with said substrate less than about 120 minutes.

16. The method according to claim 2 in which said polyisocyanate solution is in contact with said substrate 5-20 minutes.

17. The method according to claim 16 in which said polyisocyanate solution is in contact with said substrate approximately 10 minutes.

18. A method of forming a hydrophilic layer on a substrate comprising:
forming unreacted isocyanate groups on the surface of the substrate;
treating the surface of the substrate with a hydrophilic copolymer made from monomers of vinylpyrollidone and monomers containing active hydrogen adapted to form covalent bonds with the unreacted isocyanate.

19. The method of forming a hydrophilic coating according to claim 18 comprising simultaneously applying solvent solution containing polyisocyanate and hydrophilic copolymer which will form covalent bonds when reacted with isocyanates, eliminating the solvent and reacting said polyisocyanate and reactive copolymer.

20. The method according to claim 19 in which said solvent solution includes a reactive diluent which is subsequently polymerized in situ.

21. The method according to claim 20 in which a solvent is selected which will not react with isocyanates.

22. The method according to claim 20 in which said diluent in said solution is up to about 100%.

23. The method according to claim 22 in which said reactive diluent is a UV cured vinyl containing monomer, dimer or trimer.

24. The method according to claim 20 in which said reactive diluent is a UV cured, vinyl containing monomer, dimer or trimer.

25. The method according to claim 24 wherein said reactive diluent is selected from the group consisting of hydroxyl methyl methacrylate, N-vinyl-2-pyrollidone, hydroxy propylmethacrylate, acrylic, methacrylic acid and acrylamide.

26. The method according to claim 21 in which the substrate is selected from the group consisting of a vinyl or butadiene styrene rubber.

27. The method according to claim 26 including treating the substrate with chemical modifiers from the group consisting of gamma amino propyl functional silanes and ozone.

28. The method according to claim 26 including treating the substrate with a plasma discharge or high radiation energy.

29. The method according to claim 25 in which the substrate is selected from the group consisting of polyethylene and polypropylene.

30. The method according to claim 29 including treating the substrate with chemical modifiers from the group consisting of gamma amino propyl functional silanes and ozonolysis.

31. The method according to claim 30 including treating the substrate with a plasma discharge or high radiation energy.

32. The method according to claim 18 in which the copolymer has a molecular weight average of at least 100,000.

33. The method according to claim 32 in which said copolymer has at least two active hydrogen atom sites per molecule.

34. The method according to claim 33 in which said copolymer is swellable in an aqueous media.

35. The method according to claim 34 in which said copolymer is also soluble in non-aqueous solvents which do not react with isocyanates.

36. The method according to claim 18 in which said copolymer is swellable in an aqueous media.

37. The method according to claim 33 in which said copolymer is selected from the groups consisting of vinyl methyl ether, vinyl pyridine, N-vinyl-2-pyrrolidone, acrylamide, hydroxy acrylate, acrylic acid, hydroxy propylmethacrylate, and hydroxy ethyl methacrylate.

38. The method according to claim 18 in which said polyisocyanate is applied from solvent solution containing at least about 0.1% W/V polyisocyanate.

39. The method according to claim 38 in which said polyisocyanate is from about 0.3% to about 15% W/V.

40. The method according to claim 19 in which said substrate is a polymer substrate.

41. The method according to claim 40 in which said polymer substrate is selected from the group consisting of a polyurethane resin, a vinyl resin, a polyacrylate, a polycarbonate and rubber.

42. The method according to claim 41 in which copolymer has a molecular weight average of at least 100,000.

43. The method according to claim 42 in which said copolymer has an average of at least two active hydrogen atom sites per molecule.

44. The method according to claim 43 in which said copolymer is swellable in an aqueous media.

45. The method according to claim 44 in which said copolymer is also soluble in non-aqueous solvents which do not react with isocyanates.

46. The method according to claim 19 in which said copolymer is swellable.

47. The method according to claim 45 in which said copolymer is selected from the groups consisting of vinyl methyl ether, vinyl pyridine, N-vinyl-2-pyrrolidone, acrylamide, hydroxy acrylate, acrylic acid, hydroxy propyl methacrylate, and hydroxy ethyl methacrylate.

48. A biomedical product having a hydrophilic coating comprising;
a substrate;
a polyisocyanate coupling coating;
a hydrophilic copolymer coating made from monomers of vinylpyrollidone and monomers containing active hydrogen;
coating retention means for retaining said hydrophilic copolymer coating on said substrate by a covalent bond, said hydrophilic copolymer having an average of at least two or more sites capable of covalently bonding to said polyisocyanate coupling coating.

49. The product according to claim 48 in which said substrate is a polymer substrate.

50. The product according to claim 49 in which polymer substrate is selected from the group consisting of a polyurethane resin, a vinyl resin, a polyacrylate, a polycarbonate, a polyester and rubber.

51. The product according to claim 50 in which said rubber is a latex rubber, polyisoprene, or styrene butadiene.

52. A product according to claim 48 in which said substrate comprises a medical instrument adapted for blood or subcutaneous tissue contact.

53. A product according to claim 52 in which said medical instrument is an intravenous tube.

54. A product according to claim 52 in which said medical instrument is a surgical tool.

55. A product according to claim 54 in which said medical instrument is a stainless steel surgical tool.

56. A product according to claim 52 in which said medical instrument is a wound drain.

* * * * *